(12) United States Patent
Johnson et al.

(10) Patent No.: US 9,433,426 B2
(45) Date of Patent: Sep. 6, 2016

(54) ANATOMIC FEMORAL GUIDE

(71) Applicant: Smith & Nephew, Inc., Memphis, TN (US)

(72) Inventors: Darren L. Johnson, Lexington, KY (US); Gary R. McCarthy, East Bridgewater, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/732,999

(22) Filed: Jun. 8, 2015

(65) Prior Publication Data

US 2015/0265293 A1    Sep. 24, 2015

Related U.S. Application Data

(62) Division of application No. 14/177,700, filed on Feb. 11, 2014, now Pat. No. 9,078,675, which is a division of application No. 13/169,320, filed on Jun. 27, 2011, now Pat. No. 8,685,033.

(51) Int. Cl.
    *A61B 17/17*    (2006.01)
(52) U.S. Cl.
    CPC ....... *A61B 17/1764* (2013.01); *A61B 17/1714* (2013.01)
(58) Field of Classification Search
    CPC .................. A61B 17/1764; A61B 17/1714
    USPC ..................... 606/88, 96–98, 104
    See application file for complete search history.

(56) References Cited

U.S. PATENT DOCUMENTS

| 4,159,716 A | 7/1979 | Borchers |
| 5,152,764 A | 10/1992 | Goble |

(Continued)

FOREIGN PATENT DOCUMENTS

| CN | 201182625 Y | 1/2009 |
| CN | 201612662 U | 10/2010 |

(Continued)

OTHER PUBLICATIONS

Office Action issued in Chinese Application No. 2012800418967 dated Aug. 31, 2015. (Chinese original with English translation).

(Continued)

*Primary Examiner* — David Bates
(74) *Attorney, Agent, or Firm* — Burns & Levinson LLP; Joseph M. Maraia

(57) ABSTRACT

An anatomic femoral guide positions bone tunnels corresponding to the AM and PL bundles in ACL repair and reconstruction procedures. A template guide disposed in a surgical field proximate to a surgical member such as a femur or tibia defines a surgical footprint of the resulting bone tunnel. The template includes apertures corresponding to the size of the bone tunnels for the respective (AM or PL) bundles, and allows positioning at the drilling site to identify the size and location of the bone tunnel, as well as the relative distance between tunnels for double bundle procedures. An offset angle in the template provides differing orientations of the template apertures for visualizing the actual bone tunnel placement. The template has an aperture positionable parallel to a tibial plateau formation on the tibia, and the template orients a second aperture angled by the offset angle for positioning the second tunnel.

9 Claims, 10 Drawing Sheets

(56) References Cited

U.S. PATENT DOCUMENTS

| | | | |
|---|---|---|---|
| 5,520,693 | A | 5/1996 | McGuire et al. |
| 5,573,538 | A | 11/1996 | Laboureau |
| 5,575,801 | A | 11/1996 | Habermeyer et al. |
| 5,891,150 | A | 4/1999 | Chan |
| 6,254,605 | B1 | 7/2001 | Howell |
| 6,375,658 | B1 | 4/2002 | Hangody et al. |
| 7,842,042 | B2 * | 11/2010 | Reay-Young ...... A61B 17/1764 606/96 |
| 2001/0016746 | A1 | 8/2001 | McGuire et al. |
| 2002/0133165 | A1 | 9/2002 | Whittaker et al. |
| 2003/0009173 | A1 | 1/2003 | McGuire et al. |
| 2003/0216742 | A1 | 11/2003 | Wetzler et al. |
| 2006/0195112 | A1 * | 8/2006 | Ek ...................... A61B 17/1675 606/86 R |
| 2006/0271059 | A1 | 11/2006 | Reay-Young et al. |
| 2007/0233128 | A1 | 10/2007 | Schmieding et al. |
| 2008/0103506 | A1 | 5/2008 | Volpi et al. |
| 2009/0143784 | A1 | 6/2009 | Petersen et al. |
| 2009/0171355 | A1 | 7/2009 | Amis et al. |
| 2009/0216243 | A1 | 8/2009 | Re |
| 2010/0137872 | A1 | 6/2010 | Karn et al. |

FOREIGN PATENT DOCUMENTS

| | | |
|---|---|---|
| DE | 102007057075 | 5/2009 |
| FR | 2911264 | 7/2008 |
| FR | 2918554 | 1/2009 |
| JP | 2003531676 | 10/2003 |

OTHER PUBLICATIONS

International Search Report mailed Sep. 19, 2012 in corresponding International Application Serial No. PCT/US2012/043338.

Patent Examination Report No. 1 for the related Australian Patent Application No. 2012275717 issued Jan. 21, 2016.

Second Office Action from related Chinese Application No. 201280041896.7 issued Apr. 26, 2016.

Communication of the Substantive Examination Report for the related Mexican Patent Application No. MX/a/2014/000237 issued Nov. 11, 2015.

Office Action from related Russian Application No. 2014100687/14(000899) issued Apr. 15, 2016.

Office Action from related Japanese Application No. 2014-518650 issued Jun. 13, 2016.

* cited by examiner

DISPOSE, IN A SURGICAL FIELD, A SURGICAL DRILLING GUIDE INCLUDING A HOUSING HAVING A SLEEVE DISPOSED THROUGH AN APERTURE FOR MAINTAINING SLIDEABLE COMMUNICATION WITH AN INSERTION MEMBER, THE INSERTION MEMBER BEING ELONGATED AND HAVING AN AIMER TIP AND AN INSERTION KNOB FOR DISPOSING THE INSERTION MEMBER SLIDEABLY THROUGH THE HOUSING ALONG AN INSERTION AXIS
200

EXTEND AN AIMER ARM, THE AIMER ARM ENGAGING A SLOT IN THE HOUSING FOR ARCUATE MOVEMENT THERETO, THE AIMER ARM HAVING A PROXIMATE END ENGAGING THE SLOT AND AN OPPOSED DISTAL END
201

DISPOSE AN AIMER GUIDE COUPLED TO THE DISTAL END OF THE AIMER ARM, THE AIMER ARM EXTENDING IN AN INTERSECTING MANNER WITH THE INSERTION AXIS
202

AIMER ARM FURTHER COMPRISES A DIRECTOR HANDLE FOR MANIPULATION BY AN OPERATOR, THE DIRECTOR HANDLE FOR POSITIONING THE INSERTION MEMBERS ON AN OPPOSED SIDE OF A SURGICAL MEMBER FROM THE TEMPLATE FOR DRILLING BONE TUNNELS THERETHROUGH, THE HANDLE INCLUDING THE AIMER ARM, AND FURTHER COMPRISES AND AN AIMER ARM EXTENSION SLIDEABLY ENGAGING THE AIMER ARM FOR ARCUATE MOVEMENT THEREIN
203

*FIG. 4A*

POSITION, ADJACENT TO A SURGICAL MEMBER FOR DRILLING, A TEMPLATE ATTACHED TO THE AIMER GUIDE, THE TEMPLATE HAVING A FIRST APERTURE DEFINING A DRILLING FOOTPRINT ON THE SURGICAL MEMBER, THE DRILLING FOOTPRINT LOCATED ON THE INSERTION AXIS AND CORRESPONDING TO A BONE TUNNEL THROUGH WHICH A SURGICAL ATTACHMENT IS PASSED
204

TEMPLATE DEFINES THE LOCATION AND SIZE OF THE BONE TUNNEL
205

TEMPLATE HAS A FLATTENED CONSTRUCTION PROVIDING A LOW PROFILE, THE FLATTENED CONSTRUCTION FACILITATING INSERTION BETWEEN SURGICAL MEMBERS FOR DISPOSING THE TEMPLATE IN PARALLEL ALIGNMENT WITH A SURGICAL LANDMARK FOR DEFINING A LOCATION OF THE BONE TUNNEL
206

SURGICAL LANDMARK IS THE TIBIAL PLATEAU AND THE SURGICAL MEMBER IS A FEMUR, THE BONE TUNNEL EXTENDING THROUGH THE FEMUR FOR ATTACHMENT OF A SURGICAL BUNDLE REPLACEMENT
207

*FIG. 4B*

ANATOMIC FEMORAL GUIDE

CROSS REFERENCE TO RELATED APPLICATIONS

This application is a divisional of U.S. patent application Ser. No. 14/177,700 filed Feb. 11, 2014 entitled ANATOMIC FEMORAL GUIDE, which is a divisional of U.S. patent application Ser. No. 13/169,320 filed Jun. 27, 2011 entitled ANATOMIC FEMORAL GUIDE.

BACKGROUND

Reconstructive bone and ligament surgery often involves drilling into skeletal members to attach connective elements such as ligament and tendon grafts, as well as various artificial replacements and/or attachments for articulated joints. In particular, reconstructive surgery involving the anterior cruciate ligament (ACL) is becoming particularly significant because the effectiveness of reconstruction can have a profound effect on the subsequent physical abilities of the patient. For professional athletes, for example, an effective ACL repair can salvage an otherwise career ending injury. Similarly, an improperly treated ACL injury can be a permanent detriment for even everyday mobility.

Surgical procedures for reconstructing ambulatory joints, such as an ACL or PCL (Posterior Cruciate Ligament), often involve drilling bone tunnels through the femur and/or tibia. In such a procedure, although the ACL is typically referred to as a single ligament, it consists of two functional bundles, named for attachment points on the tibia. An anteromedial (AM) bundle is located more anterior (towards the front) and medial (towards the inside) of the tibia. A posterolateral (PL) bundle connects most posterior (towards the back) and lateral (towards the outside) of the tibia. Reconstructive procedures may be single bundle, directed at replacing/reconstructing one bundle or may be a double bundle procedure, focused on replacing/reconstructing both the AM and PL bundle. Each bundle requires a respective bone tunnel to be drilled in the femur.

SUMMARY

An anatomic femoral guide positions bone tunnels corresponding to the AM and PL bundles in ACL repair and reconstruction procedures. A template guide disposed in a surgical field proximate to a surgical member such as a femur or tibia defines a surgical footprint of the resulting bone tunnel. The template includes apertures corresponding to the size of the bone tunnels for the respective (AM or PL) bundles, and allows positioning at the drilling site to identify the size and location of the bone tunnel, as well as the relative distance between tunnels for double bundle procedures. An offset, or insertion, angle in the flattened template provides differing orientations of the template apertures for visualizing the actual bone tunnel placement. The template has a first aperture positionable parallel to a tibial plateau formation on the tibia, and the template orients the second aperture angled by the offset angle for positioning the second tunnel. The tibial plateau is a flattened region on the tibia opposed to the femur and is a typical anatomical reference employed in reconstructive procedures. The template has variations of aperture size and placement for defining different sized bundles and aperture spacing for defining a bone bridge between multiple tunnels.

Configurations herein are based, in part, on the observation that conventional arrangements for anatomic femoral placement of single tunnel and double tunnel locations require surgical techniques and measurements based on landmarks that may not be easy to reference. In a surgical field such as the joint area between the tibia and femur, tight clearances between bone and other tissue members tends to limit visibility and manipulative capabilities of a surgical guide for bone tunnel placement. Unfortunately, therefore, conventional techniques suffer from the shortcoming that it is difficult to identify the size and location of a femoral bone tunnel because drilling guides for ACL repair are difficult to position and do not allow visualization of the diameter and exit point of a resulting bone tunnel. Conventional procedures employ measuring objects and skill to assess the correct anatomic placement.

Configurations herein substantially overcome the above described shortcomings by employing a guide template (template) that allows the surgeon to visualize the anatomic footprint of the ACL and approximate the size of the resulting bone tunnel. The template has a flattened, low profile construction which allows positioning parallel to the tibial plateau for identifying the optimal location of the bone tunnel. The template therefore references the tibial plateau by taking a parallel orientation visible by inspection due to the flattened, planar structure of the template which is thin enough to maintain visualization of the anatomy. For a double bundle approach, the flattened template bends 15 degrees to define an insertion angle for the PL bone tunnel (second aperture in the template). As is known in the art, the double bundle approach purports to reconstruct the AM and PL bundles to original attachment points, while single bundle strives to attach to points between the former bundles. The procedure employed is based on a number of medical factors as determined by the surgeon. The disclosed guide may be employed in both so-called "outside in" or "inside out" surgical techniques. For the outside in approach, angled insertion members also ensure divergent tunnels.

The template guide system locates the anatomic femoral footprint of the ACL, for identifying hole location for the bone tunnel, double & single bundle placement, and also accommodates inside out locate tunnel placement. The template guide further allows for outside in drilling to meet anatomical insertion points. The template guide therefore allows the surgeon to see the anatomic footprint of the ACL and approximate its size, and provides a method to visualize the tunnels prior to actually drilling for both single and double bundle and for left and right knees. A pivoting linkage between the first and second (AM and PL) insertion members, or "bullets," permits a common device to be employed for both sides.

In a particular illustrated configuration, the anatomic femoral guide is a surgical drilling guide comprising a housing having a sleeve disposed through an aperture for maintaining slideable communication with an insertion member, in which the insertion member is generally elongated and has an aimer tip and an insertion knob for disposing the insertion member slideably through the housing along an insertion axis into the surgical field. An aimer arm engages a slot in the housing for arcuate movement thereto, in which the aimer arm has a proximate end engaging the slot and an opposed distal end, such that an aimer guide couples to the distal end of the aimer arm, and the aimer arm extends in an intersecting manner with the insertion axis. A template attaches to the aimer guide, in which the template has at least a first aperture defining a drilling footprint, such that the drilling footprint is located on the insertion axis and corresponds to a bone tunnel through which a surgical attachment is passed.

In a double bundle approach, the surgical drilling guide comprises a housing having a first sleeve and a second sleeve, and first and second insertion members in slideable communication with the first and second sleeves, respectively, such that the insertion members are disposed at a predetermined angle defined by the sleeves, and the insertion members each define an insertion axis and adapted for ratcheting movement towards a drilling site of a surgical member, typically a femur. The aimer arm has a proximate end slideably engaging a slot in the housing, such that the aimer arm defines an arc for arcuate movement relative to the housing. The aimer guide is removably attached to a distal end of the aimer arm, via a hinge and set screw, and the aimer guide extends toward the insertion axes defined by the insertion members. The template integrates at a distal end of the aimer guide, in which the template has a first aperture and a second aperture through a flattened surface in the template, such that each aperture defines a drilling footprint of the respective first and second insertion members. The drilling footprint therefore defines a size and location of first and second bone tunnels corresponding to the first and second insertion members, respectively, in which the flattened surface has an insertion (offset) angle between the first and second apertures for defining a relation between the first and second bone tunnels, such that the first aperture adapted for parallel alignment with a surgical landmark such as the tibial plateau.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A, 4B, 5A, and 5B depict a flowchart of an example femoral tunnel placement procedure using a particular configuration;

DETAILED DESCRIPTION

Figure 1:
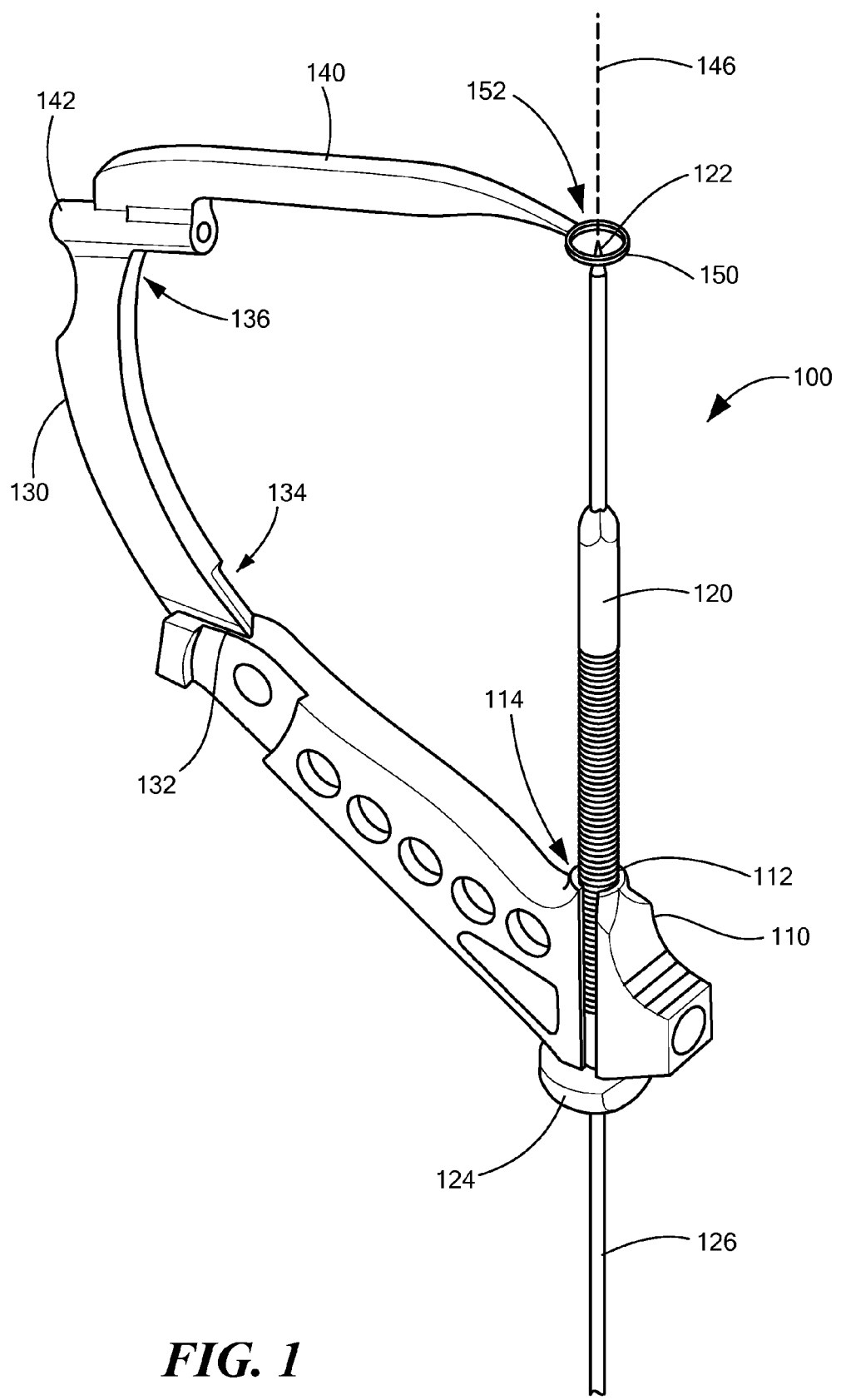
FIG. 1 shows a perspective view of the anatomic femoral guide device as disclosed herein.

The disclosures of U.S. patent application Ser. No. 14/177,700 filed Feb. 11, 2014 entitled ANATOMIC FEMORAL GUIDE, and U.S. patent application Ser. No. 13/169,320 filed Jun. 27, 2011 entitled ANATOMIC FEMORAL GUIDE, are hereby incorporated herein by reference in their entirety.

Disclosed below is an example configuration and deployment of the Anatomic Femoral Guide device for providing positioning and aiming for a surgical drilling operation. In an example arrangement, an ACL repair employing the guide device for femoral drilling is shown. Alternate configurations may employ placement on other skeletal structures, or on softer tissue surfaces, and may or may not employ a drilling approach for excavating the insertion tunnel for a guidewire.

The Anatomic Femoral Guide device (device) assists with anatomic femoral placement of single and double tunnel locations for surgical procedures such as ACL anterior cruciate ligament (ACL) and posterior cruciate ligament (PCL) repair. During such surgical procedures, accurate placement of the tunnels helps ensure effectiveness of the repair. Surgical techniques for locating the tunnels often employ measurements from landmarks that may not be easy to reference. Conventional approaches employ external measuring templates and skill to assess the correct anatomic placement of the tunnels.

The proposed approach depicts a low profile aimer which disposes a guide arm having an aimer template at a placement location of a surgical site. The template has one or more guide apertures (holes) defining placement of the tunnels, and is disposed at the placement location. Generally the template includes one or two guide apertures for single or double tunnel procedures, respectively. In contrast to conventional approaches, the template allows visualization of the size and location of the tunnels at the surgical site (the so-called "footprint" of the tunnels), and different sized templates are interchangeable with the guide arm for identifying an appropriate size. The guide apertures determine the path of an insertion guide (or "bullet") having a tip, which penetrates or marks the drilling location by advancement of the insertion guide through a corresponding guide aperture in the template. The template facilitates alignment with the tibial plateau, an anatomical feature often employed for locating the tunnels. In the case of a two tunnel approach, the template includes a second guide aperture in an angular relation to the first, such that the angle defines an appropriate or optimal orientation of the second tunnel relative to the first tunnel defined by the tibial plateau. In practice, a surgeon disposes the template such that the first guide aperture is parallel just above the tibial plateau, and the footprint of the second guide aperture defines the footprint of the second tunnel based on the angular relation of the guide apertures on the template. Therefore, the template defines 1) the number and size of tunnels, and 2) an angular relation of the footprint of the second hole to the tibial plateau (first hole), for the two tunnel approach. In practice, an angular relation of 15 degrees has been widely accepted by surgeons performing the two tunnel approach.

In an example arrangement, the template is a low profile aimer guide that can be used with or without a handle, or "director" supporting the aimer guide. For the inside out procedure, access maybe obtained through a medial portal of the knee. The correct spaced and sized single or double bundle guide is chosen, based on the intended graft size. In an inside out procedure, a pin is placed in the center of the hole or holes. For an outside in approach the correct aimer guide arm is chosen and attached to the director guide with the correct offset bullet adapter.

The insertion guides emanate from an arm or handle orienting the insertion guides along an axis through the respective guide apertures in the template. The insertion guides are movable along the axis to penetrate or mark the surgical site at the placement location defined by the template. The handle retains the insertion guides in slideable communication for axial movement, and multiple guides may be retained in a housing, which may also allow one of the insertion guides to pivot around the other while each guide axis remains focused on the placement location defined by the template. In this manner, a surgeon disposes the guide arm to position the template at the placement location, and orients the insertion guides for optimal placement of multiple (double) insertion guides by pivoting one insertion guide around the other while maintaining each along the axis defined by (through) the respective guide apertures. The housing has a bore for each insertion guide, defining a relative angle to each other and providing for divergent tunnels. Divergent tunnels are therefore assured, as well as a consistent bone bridge defined by the distance between the guide apertures.

FIG. 1 shows a perspective view of the anatomic femoral guide device as disclosed herein. Referring to FIG. 1, the guide 100 includes a housing 110 having a sleeve 112 disposed through an aperture 114 for retaining an insertion member 120. The insertion member 120, known in the art as a "bullet," has an aimer tip 122 and an insertion knob 124 for directing an insertion wire 126 to an insertion point at a surgical site, such as a bone tunnel location on a femur or tibia. An aimer arm 130 couples to the housing 110 at a proximate end 134 via a slot 132 for sliding movement therein, and may have an arc shape for arcuate movement. A guide arm 140 having a template 150 couples to a distal end 136 of the aimer arm 130, and may have a hinged connection 142 for rotation of the guide arm 140 and template 150 in the plane defined by the aimer arm 130 and insertion member 120. The template 150 includes an aperture 152 defining a drilling footprint at the surgical site, thus providing an indication of the diameter and location of a resulting bone tunnel, and the insertion member 120 defines an insertion axis 146 defining the path of the bone tunnel through the aperture 152 in the template 150.

Figure 2:
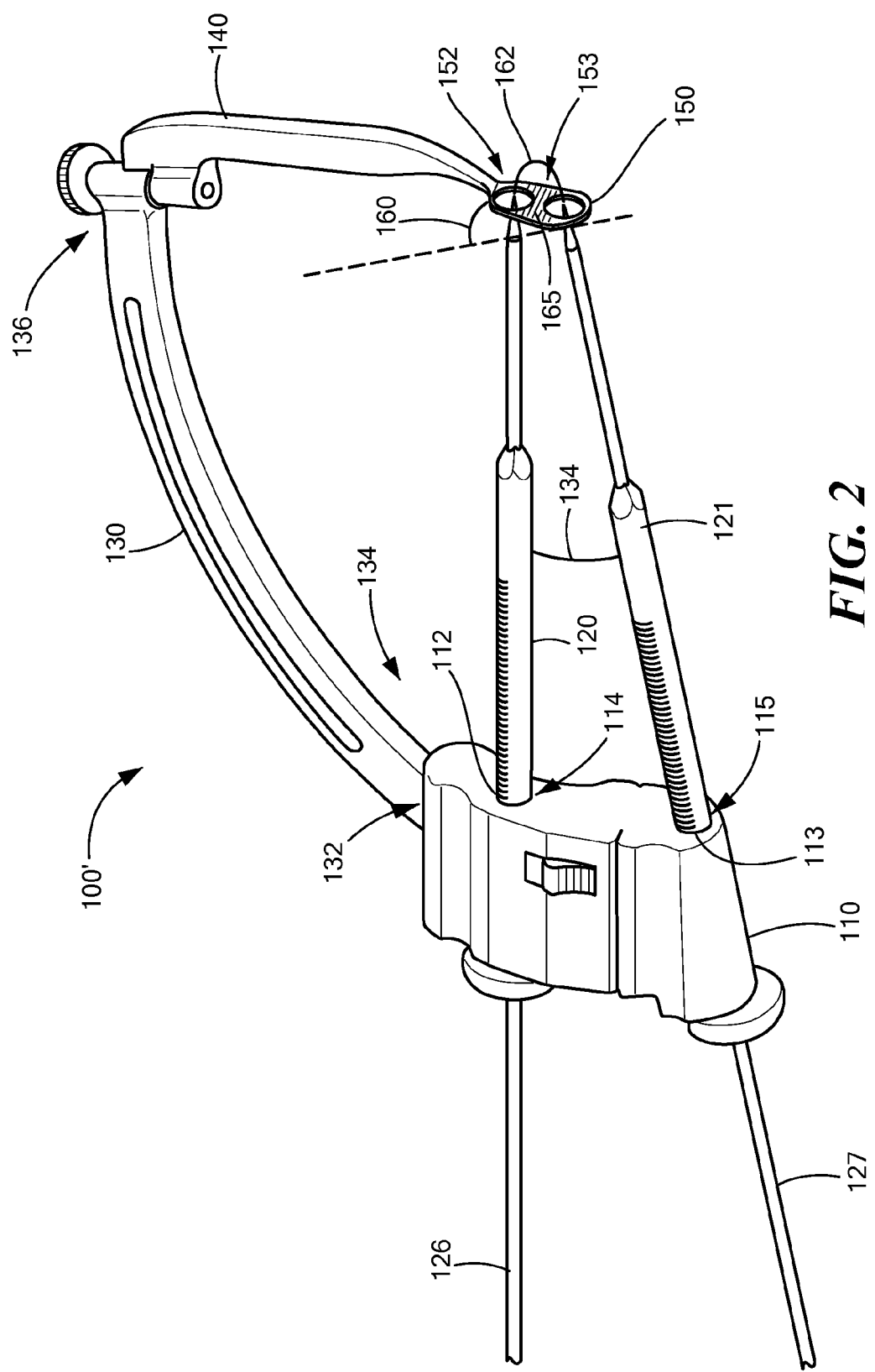
FIG. 2 shows a double bundle configuration of the anatomic femoral guide of FIG. 1.

FIG. 2 shows a double bundle configuration of the anatomic femoral guide 100 of FIG. 1. Referring to FIG. 2, an alternate configuration 100' includes a housing 110 having a plurality of insertion members 120, 121 disposed in respective sleeves 112, 113 via apertures 114, 115. A second insertion member 121 disposed at a predetermined angle 134 from the insertion member 120 directs a second insertion wire 127 to a second aperture 153. In the double bundle configuration 100', the template 150 defines an insertion angle 160 between the apertures 152, 153 resulting from an angling of the template 150 about an angular separation 162. The template 150 has a flattened, planer construction providing a low profile allowing for formation of a recognizable insertion angle 160 between the planar surface around the respective apertures 152, 153. A separation 165 between the apertures 152, 153 defines a bone bridge in the surgical member that remains between the bone tunnels following formation. A typical bone bridge is between 3-4 mm, which corresponds to a separation 165 of approximately 2-3 mm.

Figure 3:
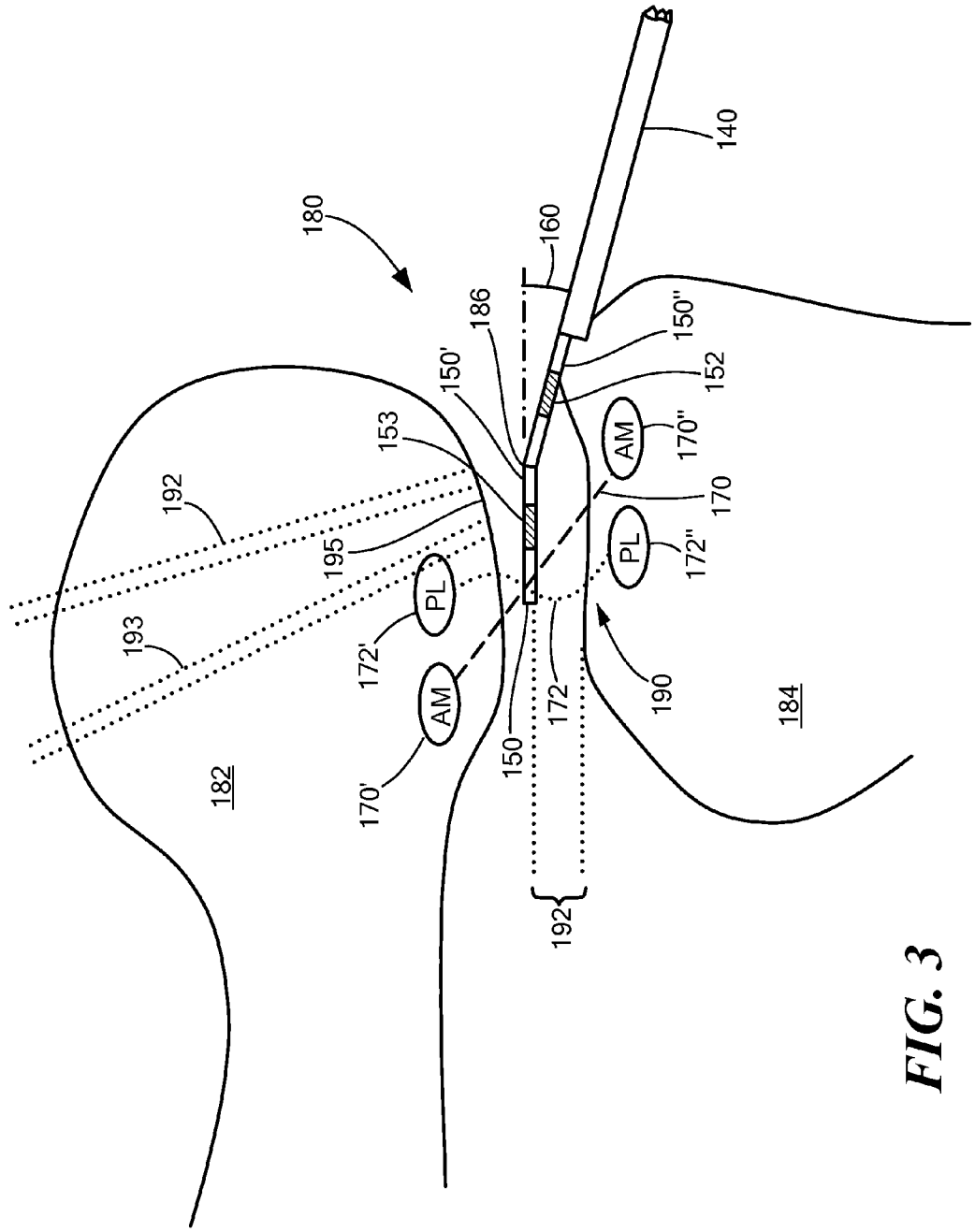
FIG. 3 shows the template of FIG. 2 deployed at a surgical site.

FIG. 3 shows the template of FIG. 2 deployed at a surgical site 180. Referring to FIGS. 1-3, the guide arm 140 (shown detached from the aimer arm 130) disposed between a femur 182 and tibia 184. The template 150 is a double bundle template such that the apertures 152 and 153 are formed in planar sections 150', 150" of the template 150 separated by a ridge 186 defining the insertion angle 160. In practice, the apertures 152, 153 correspond to tunnels used for reconstructing the AM bundle 170 and PL bundle 172 respectively, by anchoring a replacement ligament, graft, or other reconstructive member at the attachment points 170', 170" for the AM bundle and at 172', 172" for the PL bundle. In a healthy knee joint, the ACL provides stability to the knee, while also allowing for normal knee movement. The AM bundle 170 is tight when the knee is bent and provides stability in the forward (anterior) direction. The PL bundle 172 is loose when the knee is bent, and allows for rotation of the knee. When the knee is straight the two bundles are generally parallel to each other, however when the knee is bent the two bundles cross each other. Although the two bundles have slightly different functions, the bundles do not work independently, but rather they work together to keep the knee stable while still allowing dexterous movement such as during sport and exercise activity.

The template 150 is disposed such that the planer section 150' is substantially parallel to the tibial plane 190, as shown by dotted lines 192. Upon proper placement, the apertures 152, 153 are disposed in relation defined by the insertion angle 160 that they convey the surgical footprint (size and location) of the bone tunnel to be formed (drilled) by the insertion members 120, 121. Following placement of the template 150, bone tunnels 192, 193 are formed by the insertion members 120, 121 corresponding to the apertures 152, 153.

Figure 5A:
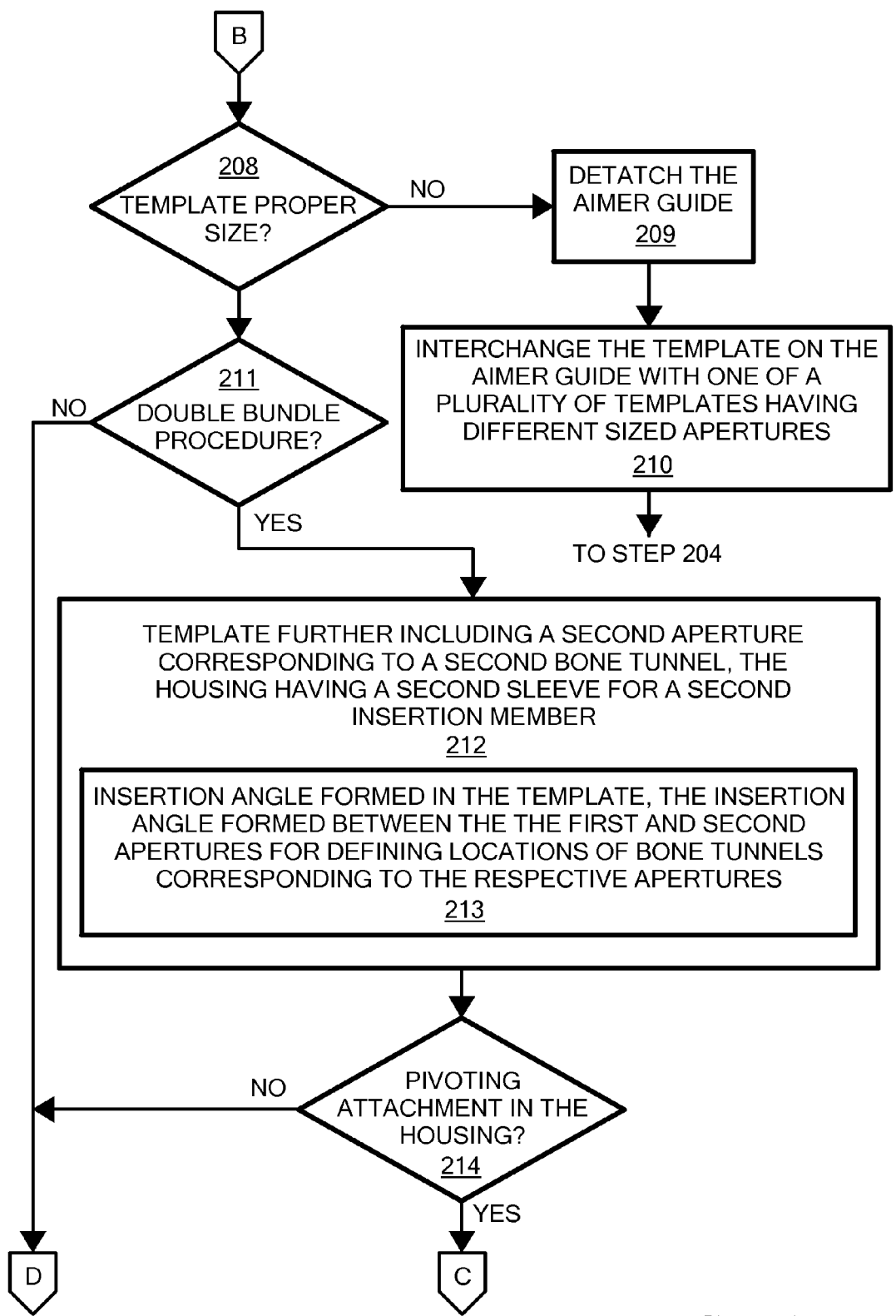
Figure 5B:
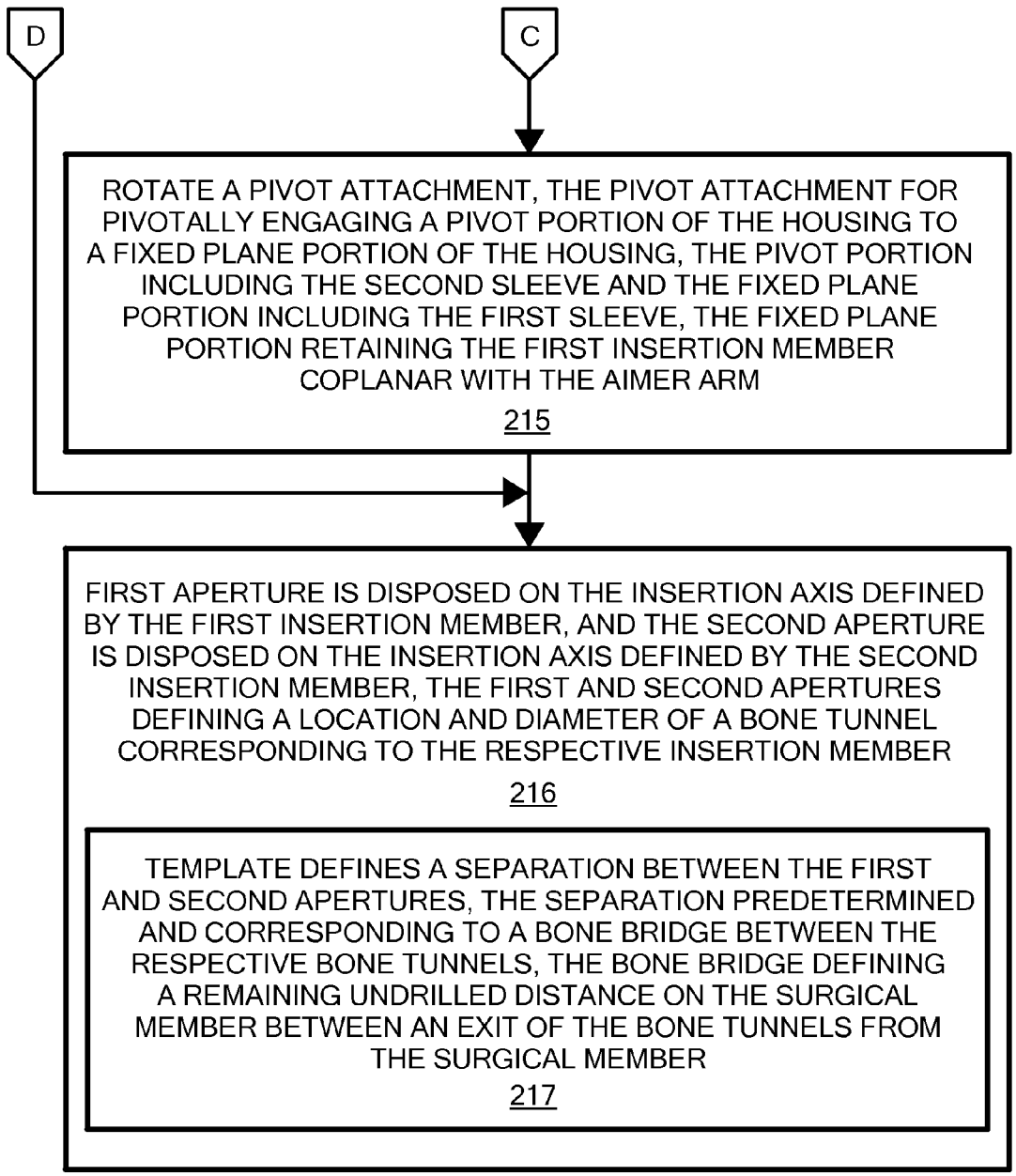

FIGS. 4 and 5 depict a flowchart of an example of femoral tunnel placement procedure using a particular configuration. The disclosed sequence depicts only an example of usage of the anatomic femoral guide as disclosed herein; other procedural sequences, options and alternatives may be pursued with the disclosed device. The example procedure depicted attempts a double bundle replacement employing a double bundle template, and defines method of surgical drilling for attaching a supportive ligament structure. Referring to FIGS. 1-5, at step 200, an operator (typically a surgeon) disposes, in a surgical field 180, a surgical drilling guide 100 including a housing 110 having a sleeve 112 disposed through an aperture 114 for maintaining slideable communication with an insertion member 120, in which the insertion member is elongated and has an aimer tip 122 and an insertion knob 124 for disposing the insertion member 120 slideably through the housing 110 along an insertion axis 146.

The surgeon extends an aimer arm 130, as the aimer arm 130 engages a slot 132 in the housing 110 for arcuate movement thereto, in which the aimer arm 130 has a proximate end 134 engaging the slot and an opposed distal end 136, as depicted at step 201. The surgeon disposes an aimer guide 140 coupled to the distal end 136 of the aimer arm 130, such that the aimer arm 130 extends in an intersecting manner with the insertion axis 146, as shown at step 202. In the example of FIG. 1, the aimer arm 130 further comprises a director handle for manipulation by an operator, such that the director handle is for positioning the insertion members 120, 120 on an opposed side of a surgical member from the template for drilling bone tunnels 192, 193 therethrough, such that the handle includes the aimer arm 130 and housing 110, and further comprising and an aimer arm extension slideably engaging the aimer arm for arcuate movement therein, as depicted at step 203.

The surgeon positions, adjacent to a surgical member 182 for drilling, a template 150 attached to the aimer guide 140, in which the template has a first aperture 153 defining a drilling footprint on the surgical member 182, such that the drilling footprint is located on the insertion axis 146 and corresponds to a bone tunnel 193 through which a surgical attachment is passed, as disclosed at step 204. The template 150 defines the location and size of the bone tunnel 192, 193, as depicted at step 205. In the example arrangement, the template 150 has a flattened construction providing a low profile, such that the flattened construction facilitates insertion between surgical members 182, 184 for disposing the template 150 in parallel alignment with a surgical landmark 190 for defining a location of the bone tunnel 192, 193, as depicted at step 206. In a particular procedure, the surgical landmark 190 is the tibial plateau and the surgical member 182 is a femur, such that the bone tunnels 192, 193 extend through the femur for attachment of a surgical bundle replacement, as disclosed at step 207.

As indicated above, the template 150 is detachable and has a range of configurations for selecting aperture 152, 153 sizes and the separation 165 defining the resulting bone bridge, typically 3-4 mm between the bone tunnels. By way of example, the template apertures 152, 153 typically range from 6-10 mm for a single bundle template, and 5/5, 5/6, 6/7, 6/8 and 7/8 for the double bundle sizes, however other sizes may be formed. A surgeon will typically select a template 150 during preparation for the surgical procedure, however the template 150 is interchangeable at any time by selecting an aimer guide 140 having the proper template 150 and apertures 152, 153. Accordingly, the surgeon can visually observe the template 150 in the joint area 180 to verify the surgical footprint, and at step 208, if the template 150 does not define an appropriate surgical footprint, may detach the aimer guide 140, as shown at step 209, and interchanging the template 150 on the aimer guide 140 with one of a plurality of templates 150 having different sized apertures 152, 153, as disclosed at step 210.

If the procedure is a double bundle procedure, as per the check at step 211, then the template 150 further includes a second aperture 153 corresponding to a second bone tunnel 193, such that the housing 110 has a second sleeve 113 for a second insertion member 121, as depicted at step 212. The second aperture 153 further defines an insertion angle 160 formed in the template, such that the insertion angle 160 is formed between the first 152 and second 153 apertures for defining locations of bone tunnels 192, 193 corresponding to the respective apertures, as shown at step 213. The insertion angle 160 is therefore a deviation from parallel between the apertures 152, 153 for visually gauging and identifying the footprint of the second bone tunnel 193 relative to the first 192, defined by a bend or deformation 186 in the flattened surface of the template 150. A complementary angular separation 162 is defined by the closed inner angle of the template 150. Typically the insertion angle is around 15 degrees, however this may change to suit preferences of the individual surgeon as providing effective feedback and reference for locating the surgical footprint.

If the housing 110 has a pivoting attachment 111, as depicted at step 214, then the procedure may further include rotating a pivot attachment 111, in which the pivot attachment is for pivotally engaging a pivot portion of the housing 110 to a fixed plane portion of the housing, such that the pivot portion includes the second sleeve 113 and the fixed plane portion includes the first sleeve 112, as the fixed plane portion retains the first insertion member 120 coplanar with the aimer arm 130, as depicted at step 215.

Continuing at step 216, the first aperture 152 is disposed on the insertion axis 146 defined by the first insertion member 120 in the surgical joint area 180, and the second aperture 153 is disposed on the insertion axis defined by the second insertion member 121, such that the first and second apertures 152, 153 define a location and diameter of a bone tunnel 192, 193 corresponding to the respective insertion member 120, 121, as shown at step 216 and in FIG. 3. In the double bundle approach, the template 150 defines a separation 165 between the first and second apertures 152, 153, in which the separation is predetermined and corresponds to a bone bridge 195 between the respective bone tunnels, the bone bridge defining a remaining undrilled distance on the surgical member 182 between an exit of the bone tunnels 192,193 from the surgical member, as depicted at step 217 In the example arrangement, the separation is about 2-3 mm for producing a bone bridge of about 3-4 mm between the tunnels 192, 193.

Figure 6:
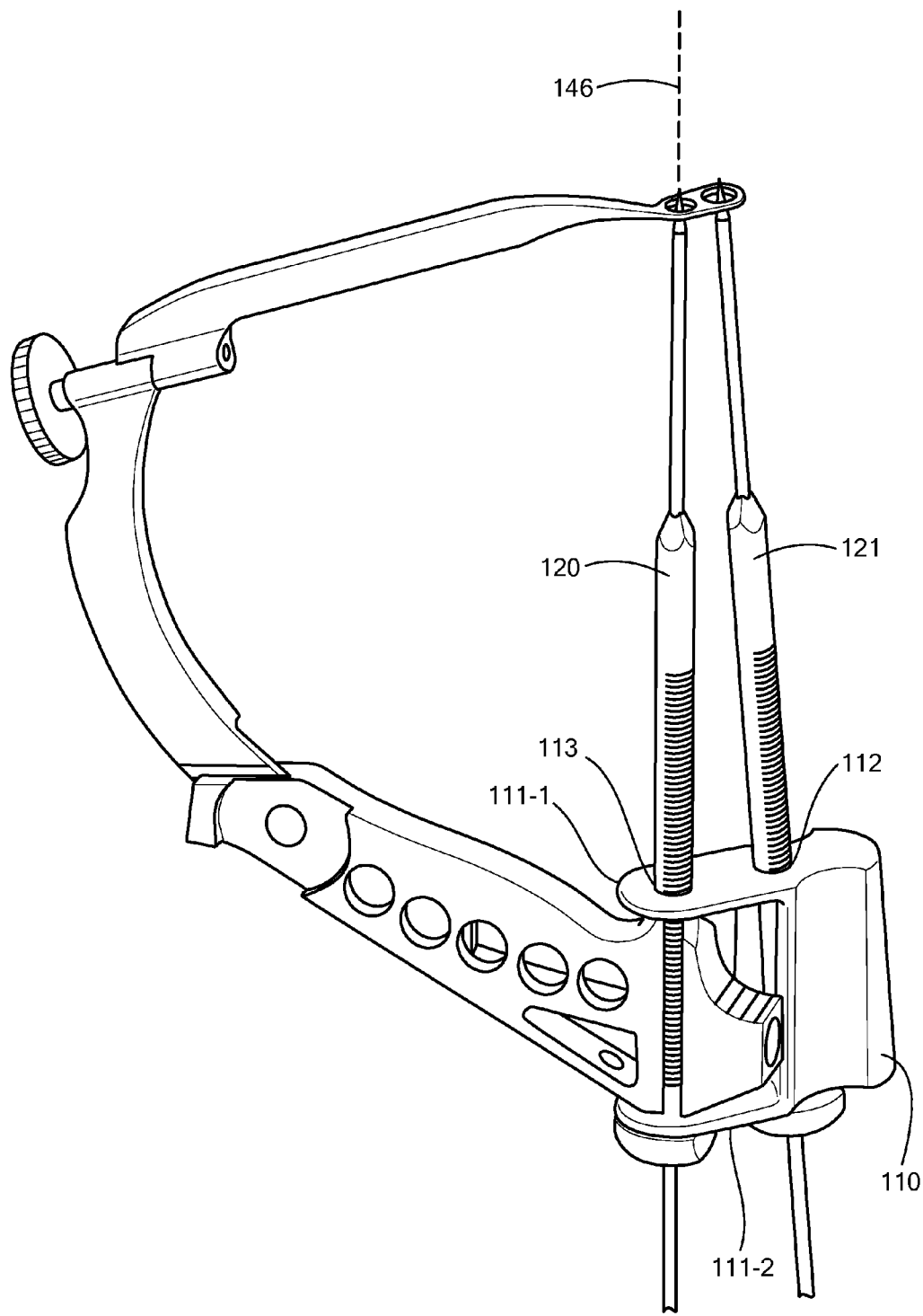
FIG. 6 shows a configuration employing a pivot connection between the first and second insertion member sleeves.

FIG. 6 shows a configuration employing a pivot connection between the first and second insertion member sleeves. Referring to FIGS. 1 and 6, pivot attachments 111-1 and 111-2 (111 generally) secure the sleeve 112 of insertion member 121 about the axis 146 through which the pivot attachments 111 pass. The portion of the housing 110 securing the insertion guide 121 is then pivotable about the insertion member 120.

Figure 7:
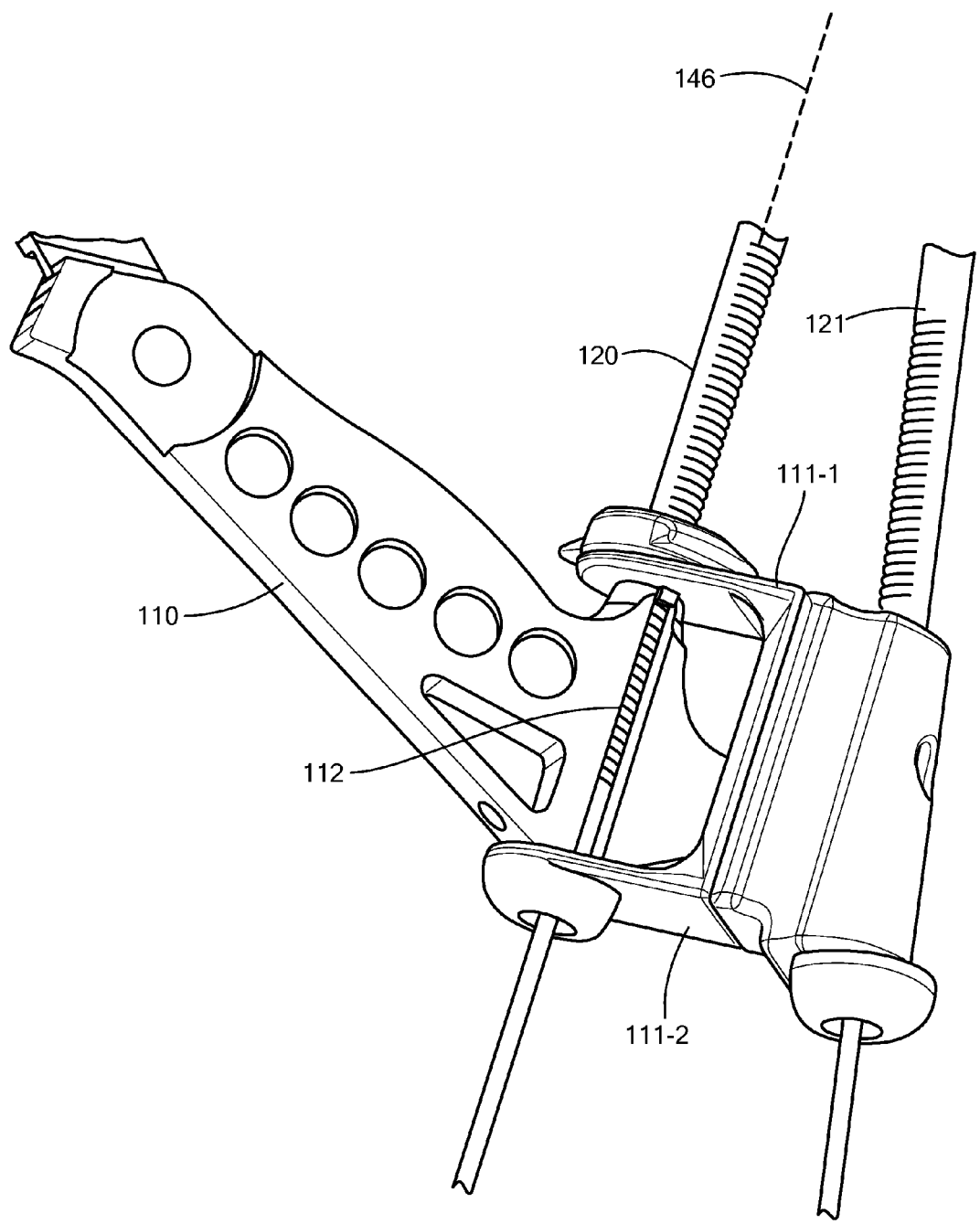
FIG. 7 shows a detail view of the pivot connection of FIG. 6.

FIG. 7 shows a detail view of the pivot connection of FIG. 6, in which the second insertion member 121 pivots around the insertion axis 146 defined by the first insertion member 120 by way of the pivot attachments 111 to secure the second insertion member in rotational communication around the sleeve 112 in the housing 110.

Figure 8:
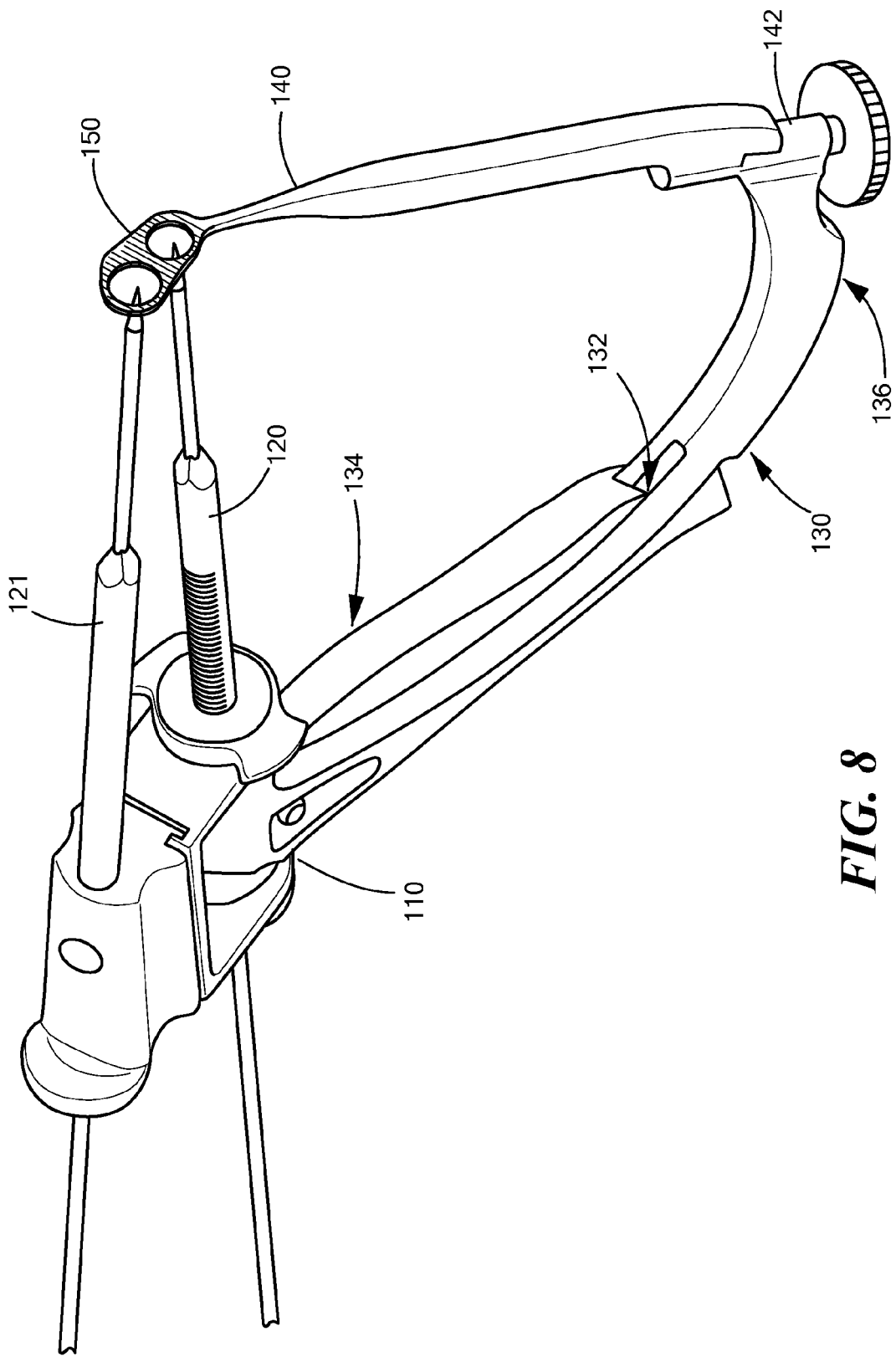
FIG. 8 shows an alternate configuration of a double bundle device as in FIG. 2 having an arced arm.

FIG. 8 shows an alternate configuration of a double bundle device as in FIG. 2 having an arced arm. Referring to FIGS. 1, 2 and 8, the aimer arm 130 has an arcuate shape as in FIG. 1 and engages a slot 132 in the housing 110 from a proximate end 132 for arcuate movement therein. The housing 110 is more elongated than the housing 110 of FIG. 2 because the slot 132 extends further toward the distal end 136 of the arm 130 for providing guidance and stability to the aimer arm 130 slidably retained therein. A hinge 142 secures the aimer guide 140 at the distal end 136 for pivoting the template 150 relative to the plane defined by the aimer arm 130 and insertion members 120, 121.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical drill guide device, comprising:
a housing having a first sleeve disposed through an aperture extending through a proximal portion thereof for maintaining slideable communication with a first insertion member, the first insertion member being elongated and having an aimer tip and an insertion knob for disposing the first insertion member slideably through the housing along a first insertion axis;
an aimer arm engaging a slot in a distal portion of the housing for arcuate movement thereto, the aimer arm having a proximate end engaging the slot and an opposed distal end;
an aimer guide coupled to the distal end of the aimer arm, the aimer arm extending in an intersecting manner with the first insertion axis;
a template attached to the aimer guide, the template having a first aperture defining a drilling footprint, the drilling footprint located on the first insertion axis and corresponding to a first bone tunnel through which a surgical attachment is passed; and
a pivot member pivotally engaging the proximal portion of the housing, the pivot member having a second sleeve disposed through an aperture therethrough for maintaining slideable communication with a second insertion member, the second insertion member being elongated and having an aimer tip and an insertion knob for disposing the second insertion member slideably through the pivot member along a second insertion axis, wherein the template has a flattened construction providing a low profile, the flattened construction facilitating insertion between surgical members for disposing the template in parallel alignment with a surgical landmark for defining a location of the bone tunnel, wherein the template further comprises a second aperture corresponding to a second bone tunnel, and an insertion angle formed between the first and second apertures for defining locations of the first and second bone tunnels corresponding to the respective apertures; and wherein the proximal portion of the housing retains the first insertion member coplanar with the aimer arm.

2. The device of claim 1 wherein the template defines the locations and sizes of the first and second bone tunnels, the aimer guide being detachable for interchanging a plurality of templates having different sized apertures.

3. The device of claim 1 wherein the surgical landmark is the tibial plateau and one of the surgical members is a femur, one of the first and second bone tunnels extending through the femur for attachment of a surgical bundle replacement.

4. The device of claim 1 wherein the first template aperture is disposed on the first insertion axis defined by the first insertion member, and the second template aperture is disposed on the second insertion axis defined by the second insertion member, the first and second template apertures defining the locations and diameters of the first and second bone tunnels corresponding to the respective first and second insertion members.

5. The device of claim 1 wherein the template defines a separation between the first and second template apertures, the separation being predetermined and corresponding to a bone bridge between the respective first and second bone tunnels, the bone bridge defining a remaining undrilled distance on one or more surgical members between exits of the first and second bone tunnels from the respective surgical members.

6. The device of claim 1 wherein the pivot member comprises a first pivot attachment having a first through hole aligned with an upper opening of the aperture of the proximal portion of the housing and a second pivot attachment having a second through hole aligned with a lower opening of the aperture of the proximal portion of the housing.

7. The device of claim 1 wherein the first sleeve disposed through the aperture of the proximal portion of the housing comprises the first sleeve disposed through the first through hole of the first pivot attachment.

8. The device of claim 7 wherein the first and second pivot attachments secure the second sleeve of the second insertion member about the first insertion axis through which the first and second pivot attachments pass.

9. The device of claim 1 wherein the pivot member is pivotable about the first insertion member.

* * * * *